US012797203B2

(12) United States Patent
Link et al.

(10) Patent No.: US 12,797,203 B2
(45) Date of Patent: Nov. 17, 2026

(54) INTERPHALANGEAL JOINT IMPLANT

(71) Applicant: WALDEMAR LINK GmbH & Co. KG, Hamburg (DE)

(72) Inventors: Helmut D. Link, Hamburg (DE); Hans-Joachim Fischer, Norderstedt (DE); Jan Teuber, Norderstedt (DE)

(73) Assignee: WALDEMAR LINK GmbH & Co. KG, Hamburg (DE)

( * ) Notice: Subject to any disclaimer, the term of this patent is extended or adjusted under 35 U.S.C. 154(b) by 950 days.

(21) Appl. No.: 18/002,679

(22) PCT Filed: Jun. 25, 2021

(86) PCT No.: PCT/EP2021/067500
§ 371 (c)(1),
(2) Date: Dec. 21, 2022

(87) PCT Pub. No.: WO2021/260183
PCT Pub. Date: Dec. 30, 2021

(65) Prior Publication Data

US 2023/0320862 A1 Oct. 12, 2023

(30) Foreign Application Priority Data

Jun. 26, 2020 (EP) .................................... 20182547

(51) Int. Cl.
*A61F 2/42* (2006.01)
*A61F 2/30* (2006.01)

(52) U.S. Cl.
CPC .. *A61F 2/4241* (2013.01); *A61F 2002/30624* (2013.01); *A61F 2002/4243* (2013.01)

(58) Field of Classification Search
CPC ......... A61F 2/42; A61F 2/4225; A61F 2/4241
See application file for complete search history.

(56) References Cited

U.S. PATENT DOCUMENTS 3,805,302 A * 4/1974 Mathys ................. A61F 2/4241 446/376
3,869,729 A 3/1975 Attenborough
(Continued)

FOREIGN PATENT DOCUMENTS

CN 101325927 A 12/2008
CN 204562343 U 8/2015
(Continued)

OTHER PUBLICATIONS

International Search Report and Written Opinion mailed Oct. 7, 2021, in connection with International Patent Application No. PCT/EP2021/067500, 10 pgs.
(Continued)

*Primary Examiner* — Marcia L Watkins
(74) *Attorney, Agent, or Firm* — Chiesa Shahinian & Giantomasi PC

(57) ABSTRACT

The present disclosure provides a joint implant for replacing a finger joint. The joint implant includes a first component, wherein the first component includes a first joint section and a first anchoring section, the first joint section including a concave joint surface about a first axis and the first anchoring section extending transverse to the first axis. The joint implant also includes a second component, wherein the second component includes a second joint section and a second anchoring section, the second joint section including a circumferential surface about a second axis and the second anchoring section extending transverse to the second axis, wherein the circumferential surface includes a convex joint surface that is configured to act as a hinge joint with the concave joint surface of the first joint section.

18 Claims, 3 Drawing Sheets

(56) References Cited

U.S. PATENT DOCUMENTS

| | | | | | |
|---|---|---|---|---|---|
| 4,213,208 | A * | 7/1980 | Marne | A61F 2/4225 623/21.16 |
| 4,304,011 | A * | 12/1981 | Whelan, III | A61F 2/4241 623/21.16 |
| 4,352,212 | A * | 10/1982 | Greene | A61F 2/4241 623/21.16 |
| 5,147,386 | A * | 9/1992 | Carignan | A61F 2/4241 623/21.16 |
| 5,443,516 | A | 8/1995 | Albrektsson et al. | |
| 5,667,510 | A | 9/1997 | Combs | |
| 5,702,471 | A | 12/1997 | Grundei et al. | |
| 6,656,178 | B1 | 12/2003 | Veldhuizen et al. | |
| 7,625,379 | B2 | 12/2009 | Puno et al. | |
| 9,464,561 | B2 | 10/2016 | Shemwell et al. | |
| 9,622,783 | B2 | 4/2017 | Reiley et al. | |
| 9,675,392 | B2 | 6/2017 | Shemwell et al. | |
| 10,357,260 | B2 | 7/2019 | Triplett et al. | |
| 11,266,450 | B2 | 3/2022 | Link et al. | |
| 2004/0167625 | A1 | 8/2004 | Beyar et al. | |
| 2004/0260289 | A1 | 12/2004 | Padget et al. | |
| 2007/0156241 | A1 | 7/2007 | Reiley et al. | |
| 2007/0282443 | A1 | 12/2007 | Globerman et al. | |
| 2010/0125301 | A1 | 5/2010 | Kinmon et al. | |
| 2011/0118796 | A1 | 5/2011 | Reiley et al. | |
| 2013/0066435 | A1 | 3/2013 | Averous et al. | |
| 2013/0131822 | A1 | 5/2013 | Lewis et al. | |
| 2015/0073413 | A1 | 3/2015 | Palmer et al. | |
| 2015/0223856 | A1 | 8/2015 | Tyber et al. | |
| 2016/0367300 | A1 | 12/2016 | Caldarella et al. | |
| 2017/0007416 | A1 | 1/2017 | Sander et al. | |
| 2017/0181770 | A1 | 6/2017 | Reiley et al. | |
| 2017/0348032 | A1 | 12/2017 | Barry et al. | |
| 2020/0179019 | A1 | 6/2020 | Link et al. | |

FOREIGN PATENT DOCUMENTS

| | | | |
|---|---|---|---|
| CN | 205339255 | U | 6/2016 |
| CN | 106344218 | A | 1/2017 |
| DE | 69002159 | T2 | 10/1993 |
| DE | 29813030 | U1 | 10/1998 |
| DE | 10354601 | B3 | 6/2005 |
| DE | 202009008872 | U1 | 9/2009 |
| DE | 102013210638 | B4 | 3/2018 |
| EP | 1096906 | A1 | 5/2001 |
| EP | 2158864 | A2 | 3/2010 |
| EP | 3928747 | A1 | 12/2021 |
| WO | 2014/195446 | A1 | 12/2014 |
| WO | 2015/147846 | A1 | 10/2015 |
| WO | 2018/188861 | A1 | 10/2018 |
| WO | 2020/076376 | A1 | 4/2020 |

OTHER PUBLICATIONS

Markforged, "3D Printed Joinery: Simplifying Assembly", retrieved online at https://markforged.com/resources/blog/joinery-onyx, 2025, 23 pgs.

Non-Final Office Action mailed Aug. 27, 2025, in connection with U.S. Appl. No. 18/765,571, filed Jul. 8, 2024, 25 pgs.

Notice of Allowance and Fee(s) due mailed Apr. 2, 2024 in connection with U.S. Appl. No. 18/250,766, filed Apr. 27, 2023, 22 pgs.

International Search Report and Written Opinion mailed Jan. 28, 2022, in connection with International Patent Application No. PCT/EP2021/077686, 13 pgs.

Invitation to Pay Additional Fees mailed Dec. 7, 2021, in connection with International Patent Application No. PCT/EP/2021/077686, 9 pgs.

Office Action mailed Mar. 3, 2021, in connection with Chinese Patent Application No. 201880023361.4, 12 pgs. (including translation).

International Search Report and Written Opinion mailed Jun. 12, 2018 in connection with International Application No. PCT/EP2018/055899, 19 pgs. (including translation).

Non-Final Office Action mailed Dec. 19, 2023 in connection with U.S. Appl. No. 18/250,766, filed Apr. 27, 2023, 23 pgs.

* cited by examiner

INTERPHALANGEAL JOINT IMPLANT

CROSS-REFERENCE TO RELATED APPLICATIONS

This application is a National Stage under 35 U.S.C. 371 of International Patent Application No. PCT/EP2021/067500, filed Jun. 25, 2021, which claims priority from European Patent Application No. 20182547.8, filed Jun. 26, 2020; the disclosure of all of which are incorporated herein by reference in their entirety.

TECHNICAL FIELD

The invention relates to a joint implant, in particular a joint implant for replacing an interphalangeal joint of a foot or a hand, and a method of assembling such a joint implant.

BACKGROUND OF THE INVENTION

Functional disorders of interphalangeal joints can be caused on the one hand by arthritis. One of the most common forms of arthritis is arthrosis. In case of arthrosis, the disease leads to "wear and tear" of the joint cartilage, which in turn results in an incorrect loading of the joint and further changes to the joint surfaces. The patient experiences this in form of a painful restriction or even elimination of joint function. Dysfunctions of the interphalangeal joints can also result from injury, e.g. a luxation or a fracture of the joint. Primary treatment of a joint fracture likely leads to post-traumatic arthrosis of the joint with the previously noted consequences.

One way to eliminate the pain caused by the above-mentioned functional disorders is to stiffen the joint. Although this makes the pain disappear, it also means the disappearance of the joint's movability.

Another way to eliminate this pain is to implant a joint implant. Such a joint implant may be inserted via a lateral, dorsal or palmar access. A finger joint implant that is implanted using a dorsal access is the SWANSON flexible finger joint implant.

Another joint implant that has also been implanted laterally as a replacement of a proximal interphalangeal joint is the Digitos finger joint implant of OSTEO AG. Lateral access has the advantage to preserve the soft tissue on the dorsal and palmar side of the finger. For implanting this finger joint implant the inner collateral ligament on the finger phalanx is detached. Then, the joint is luxated laterally and a part of the palmar plate is detached. Afterwards, the head of the first finger phalanx and the base of the second finger phalanx is resected so that a predetermined distance is created between the two finger phalanxes. A rectangular space extending along its central axis is then rasped into each finger phalanx and a shaft is cemented into this rectangular space. The joint elements are then attached to the anchored shaft and are positioned to insert an axis into aligned openings of the joint elements for enabling articulation of the finger phalanxes relative to each other.

Since the middle finger joint has to be luxated laterally during implantation of such a finger joint prosthesis, the extensor tendon apparatus, the two flexor tendons and the collateral ligaments of the joint are affected. It was found that this likely leads to a later impairment of the joint replacement's function. In addition, a large amount of bone substance was sacrificed for the implantation of the finger joint implant because a shaft had to be inserted in the direction of the central axis of the finger joints.

A significantly improved finger joint implant is known from EP 1 096 906 A1. The design of this implant enables a surgical procedure, in which the finger joint implant can be implanted laterally into a prepared recess at the finger joint to be replaced. This considerably simplifies implantation and allows to preserve the ligaments and tendons except for the collateral ligament that is removed to create the lateral access for insertion of the finger joint implant.

Although such finger joint implants already allow significantly less damage to the surrounding tissue during surgery and therefore a much faster healing, it has been shown in practice that the axis of the finger joint is not fixed in position but moves to a small extent in the longitudinal direction of the finger. It is assumed that over time, this movement can cause loosening, increased amounts of wear or even fracture of the joint implant.

DE 10 2013 210 638 B4 proposes a finger joint implant that addresses this problem. The configuration of the finger joint implant is similar to the configuration of the finger joint implant disclosed in EP 1 096 906 A1. It comprises two anchoring strips, one for each finger phalanx. One of the anchoring strips comprises at one end a hollow cylinder whereas the other one the anchoring strips comprises at one end an insertion element that cooperates with the hollow cylinder as a hinge joint. The latter anchoring strip is connected to the insertion element via a pin that is inserted into a hole of the insertion element. The pin-hole connection allows a relative movement along the longitudinal axis of the pin. Thus, the axis of the hinge joint is able to shift.

Nonetheless, the inventors realized that the kinematics acting on this modified finger joint implant after surgery seems to still cause a load situation that is disadvantageous for this joint. More specifically, there appears to be an unequal loading, which in turn may cause increased wear of the joint surfaces or loosening of the joint. Surgery may exacerbate this effect by changing how loads are acting on the joint surfaces of the implant.

Further, bone ingrowth in the vicinity of or even between the moving parts of finger joint implants has been observed. This may also occur in case of native joints in the form of osteophytes. This bone ingrowth likewise bears the risk of causing complications concerning the functionality of the finger joint implant.

Moreover, finger joint prostheses are inherently very delicate structures due the anatomy at the implantation site. Thus, stress concentrations caused by an unbalanced loading of a finger joint implant increase the risk of failure of the implant. In this respect, the artificial finger joint may fracture short-time due to an overload or long-term due to fatigue.

SUMMARY

Thus, it has been an objective of the present disclosure to provide a finger joint implant that addresses above-noted problems. In particular, it has been an objective to increase the lifetime of the finger joint implant and to better protect the functionality of the finger joint implant from bone growth in the vicinity of the joint. It has also been an objective to improve anchorage of the finger joint implant.

In view of this, the disclosure provides a joint implant for replacing an interphalangeal joint. The interphalangeal joint may be an interphalangeal finger joint or an interphalangeal foot joint. The joint implant comprises a first component and a second component.

The first component includes a first joint section and a first anchoring section, wherein the first joint section comprises a concave joint surface about a first axis and the first anchoring section extends transverse to the first axis.

The second component includes a second joint section and a second anchoring section, wherein the second joint section comprises a circumferential surface about a second axis. The second anchoring section extends transverse to the second axis. The circumferential surface includes a convex joint surface that is configured to act as a hinge joint with the concave joint surface of the first joint section.

The second component further comprises a bone shield arranged between the second joint section and the second anchoring section. The bone shield extends about a third axis and partially covers the circumferential surface of the second joint section with a gap being formed between the circumferential surface and the bone shield.

The concave joint surface forms a recess for accommodating a part of the circumferential surface of the second joint section.

Consequently, the first anchoring section extends from a side opposite to the concave joint surface so that the space between the first axis and the concave joint surface may accommodate the second joint section. The convex joint surface of the second joint section faces the concave joint surface of the first joint section for forming the hinge joint.

Since the bone shield extends about a third axis and partially covers the circumferential surface of the second joint section, the bone shield preferably comprises a concave inner surface that faces the circumferential surface of the second joint section.

The bone shield being arranged between the second joint section and the second anchoring section rotates during flexion and extension of the finger joint implant as part of the second component relative to the first component.

Opposite to the inner surface of the bone shield, the bone shield comprises an outer surface from which the second anchoring section extends from in a traverse direction to the third axis.

The bone shield particularly covers a portion of the circumferential surface of the second component that does not act as convex joint surface or as a hinge joint with the concave joint surface of the first joint section.

In other words, the bone shield covers and protects the portion of the circumferential surface of the second joint section that is not intended to be in contact with the concave joint surface of the first joint section but rotates relative to this section.

The bone shield covers the circumferential surface of the second joint section in a circumferential direction and in a width direction of this surface.

The bone shield acts as a protection. On the one hand, the bone shield prevents soft tissue to interfere with the function of the joint. For example, it prevents the joint from being hindered due to soft tissue entering the joint gap along the circumferential surface of the second joint section. On the other hand, the bone shield protects surrounding tissue from being adversely affected by the joint sections of the joint moving relative to each other. In particular, the bone shield prevents bone tissue from growing into the joint gap or joint space.

The gap between the circumferential surface of the second joint section and the inner surface of the bone shield provides a space that allows fluid, in particular synovial fluid, to enter. Thus, this space acts as a reservoir for fluid that may assist in lubricating the joint implant. The bone shield and, thus, the gap being formed between the circumferential surface and the bone shield, is preferably adjacent to the convex joint surface of the second joint section so that fluid can be provided to and received from the joint surface. This flow of fluid also prevents the liquid film from being interrupted due to the movement of the joint and, thus, assists in keeping joint friction comparatively low.

Consequently, the gap is preferably at least present at both ends of the bone shield in a circumferential direction, i.e. at least partially along the edges of the bone shield facing in the circumferential direction (or extending transverse to the circumferential direction).

Preferably, the second joint section is connected to the bone shield via a compensation mechanism. The compensation mechanism allows for a relative movement between the second joint section and the bone shield in relation to a fourth axis, the fourth axis being transverse to the second axis (and the third axis) of the second joint section.

A native interphalangeal joint acts like a hinge joint, which is why the joint implant is generally configured to act as such. Nonetheless, interphalangeal joints are not moving like perfect hinge joints but, instead, allow for rotational and translational movability or slack of opposing bones relative to each other.

Although the rotational movement imitating a hinge joint has the largest range of motion, a finger joint also comprises a range of motion about an axis transverse to the hinge joint axis (i.e. running along the finger bone or along a longitudinal direction of the anchoring section). Further, the distance between opposing bones of an interphalangeal joint may also differ as a function of the joint's rotational position. It is believed that this difference between an ideal hinge joint and a native interphalangeal joint is the cause of an increase in wear that particularly takes place at the lateral edges of finger joint implants known from the prior art.

Consequently, the compensation mechanism allowing for a relative movement between the second joint section and the bone shield in relation to a fourth axis that extends transverse to the second axis has the advantage to provide a joint implant that imitates the movability of a native finger joint more closely. As a result, the adaptation of the joint implant to the kinematic environment of the resected native joint is enhanced and allows for a reduction in wear of the joint surfaces and, thus, a longer service life of the joint implant.

In other words, the compensation mechanism allows for a change in length of the second component and/or the relative orientation between the bone shield and the second anchoring section on one side and the second joint section on the other side. Thus, the compensation mechanism has the function to compensate by rotating and/or translating instead of the joint implant having to bear such loads (i.e. to give in instead of resisting).

The compensation mechanism preferably comprises a pin and a hole, wherein the pin and the hole are configured for a relative movement along and/or about the fourth axis.

The pin of the compensation mechanism is arranged on the side of one of the second joint section and the bone shield and the hole is arranged on the side of the other one of the second joint section and the bone shield.

The pin is preferably integrally formed with the second joint section, the bone shield, or the second anchoring section.

The hole may be formed as a through hole or a blind hole. Being formed as a through hole has the advantage of allowing a smooth and constant translation. If being shaped as a blind hole, pressure may build up at the bottom of the hole that may cause resistance when translating and provides a dampening effect.

The pin and the hole establish a simple mechanism for a relative movement along and/or about the fourth axis. In this mechanism, the longitudinal axis of the pin and the fourth axis are in particular parallel to each other and are preferably aligned. The same applies for the longitudinal axis of the hole that interacts with the pin.

A relative movement along the fourth axis between the second joint section on one side and the bone shield and the second anchoring section on the other side allows for modifying the length of the second component and, thus, the longitudinal extension of the joint implant (i.e. the gap between the opposing ends of the adjacent bones). The longitudinal extension is to be understood to be along the joint implant in the proximal-distal direction. The longitudinal extension may be defined as an extension perpendicular to the first axis and along the first anchoring section and the second anchoring section. The longitudinal extension may be understood as the allover length of the joint implant.

Consequently, the relative movement of the first component and the second component along the fourth axis advantageously adapts to a change in distance of opposite bones and, thus, adapts to the flexion or extension by a change in length of the second component. Since the mechanism is able to compensate such a change in distance between adjacent phalanges, a load acting on the joint can be reduced or even eliminated. As a result, the loading of the implant is reduced, which enhances the service life of the implant.

The same applies to a relative rotation about the fourth axis between the second joint section on the one side and the bone shield and the second anchoring section on the other side. Instead of causing torsional stress within the joint implant, the compensation mechanism prevents such a stress from occurring by adjusting the second component with a relative rotation between the hole and the pin about the fourth axis.

Preferably, the gap is formed between the circumferential surface of the second joint section and an inner surface of the bone shield by a difference in their profiles.

The difference in profile of the circumferential surface of the second joint section in a cross section along the second axis in relation to the profile of the inner surface of the bone shield along the third axis provides a gap between these surfaces that allows for a relative rotation between the second joint section and the bone shield about the fourth axis.

For example, in an initial position of the second joint section relative to the bone shield, the second axis and the third axis may be defined as basically being aligned with or parallel to each other. In case the compensation mechanism allows for a relative translation between the second joint section and the bone shield, the initial position may also be defined as the closest arrangement between the bone shield and the second joint section, i.e. as the shortest extension (allover length) of the second component. In this initial position, the bone shield is able to rotate about the fourth axis relative to the second joint section so that the second axis and the third axis are inclined relative to each other.

In order to allow for this relative rotation, there is a difference in profile in a cross-section along as well as perpendicular to the second and third axes (for example, as seen in the initial position). In other words, the circumferential surface and the inner surface differ in shape to provide a gap that allows for a rotation about the fourth axis.

Since the rotation is about the fourth axis, this gap is present in planes that are perpendicular to the fourth axis. These cross-sectional planes show a gap that extends (at least partially) between and along the inner surface of the bone shield and the circumferential surface of the second joint section.

Preferably, this difference in profiles or shapes provides a gap that increases in width towards the ends of the bone shield along the third axis (or the ends of the second joint section along the second axis). This gap provides room for a relative rotation about the fourth axis. It also defines the range of motion of the bone shield relative to the second joint section about this axis.

The width of the gap is defined as the shortest distance between a point on one of the inner surface of the bone shield and the circumferential surface of the second joint section and the surface of the other one of the inner surface of the bone shield and the circumferential surface of the second joint section.

Further, the gap preferably increases in width towards the end(s) of the inner surface of the bone shield in a circumferential direction. In other words, in the aforenoted initial position, the widest gap between the circumferential surface of the second joint section and the inner surface of the bone shield may be located at the ends of the gap along the second and third axes at the circumferential ends of the gap.

Preferably, the profile of the circumferential surface in a cross-section along the second axis is faceted.

In other words, the profile of the circumferential surface is faceted or comprises facets (linear sections) in a cross-section along the second axis so that the distance of the circumferential surface to the inner surface of the bone shield, i.e. the gap, increases towards the end(s) of the circumferential surface in the direction of this axis. In other words, the cross-section of the second joint section along the second axis becomes smaller towards the end(s).

Although the profile of the circumferential surface is preferably faceted, it may alternatively be faceted and/or curved in order to achieve aforenoted configuration of the gap between the circumferential surface and the inner surface of the bone shield.

Preferably, the convex joint surface is arranged in a middle portion and in between two tapered sections of the circumferential surface, wherein the tapered sections limit the relative rotation of the bone shield and the second joint section about the fourth axis.

Here, the convex joint surface arranged about the second axis provides the joint function in cooperation with the concave joint surface of the first joint section in the central or middle portion along the second axis of the second component. Thus, the circumferential surface has a faceted profile at least at the tapered sections on both sides of the convex joint surface. Preferably, the entire profile is faceted, i.e. the profile basically consists of linear sections. The tapered sections define a stop for the relative rotation between the inner surface of the bone shield and the circumferential surface of the second joint section about the fourth axis. Although the stop may be established by a contact point, the profile is preferably configured for a line contact or a surface contact. This reduces contact pressure at the stop.

As a result, the distribution of loads in the end positions about the fourth axis is enhanced and, thus, the service life of the implant. Further, an abutment of these surfaces defines the leeway of the joint about the fourth axis that prevents high loads caused by the kinematic environment and at the same limits the movability of the joint to a defined extent so that a patient does not experience discomfort.

In particular, the relative rotation of the bone shield and the second joint section about the fourth axis is limited to approximately ±2° to ±10°, preferably approximately ±4° to ±6°, and most preferably approximately ±5°.

This is achieved by the shape and dimensions of the inner surface of the bone shield and the shape and dimensions of the tapered sections (and the convex joint surface in between). Thus, the inner surface of the bone shield and the circumferential surface of the second joint section are configured to abut at above noted angular ranges about the fourth axis.

These ranges provide movability aside from the hinge-joint in order to adapt to the kinematic environment of a patient's anatomy and as a result, reduce the forces acting on the artificial joint.

Preferably, the bone shield forms at least one abutment surface facing in a circumferential direction in relation to the third axis for limiting flexion or extension of the joint implant.

Consequently, the bone shield further defines the range of motion of the joint implant besides its above-described protective function. In particular, such an abutment surface abuts against an opposite abutment surface comprised by the first joint section. Consequently, each abutment surface of the bone shield abuts a corresponding surface that is preferably arranged at the second joint section and is even more preferably integral to the second joint section.

The abutment between the abutment surface of the bone shield and an abutment surface of preferably the second joint section facing in the opposite direction to the surface of the bone shield thus defines the maximum deflection of the joint in flexion and/or extension.

Preferably, the bone shield comprises two abutment surfaces facing in opposite circumferential directions, wherein one pair of abutment surfaces limits flexion whereas the other pair of abutment surfaces limits the extension of the joint.

In any case, such an abutment surface (or pair of abutment surfaces) effectively limits flexion and/or extension of the joint despite having a simple preferably integral configuration. In this way, it complements the functionality of the joint implant.

Preferably, the range of motion of the joint implant in flexion-extension is about 90° to 110° and preferably about 100°.

By providing such a range of motion to the joint implant, such a joint implant in turn provides a functionality that is very close to or even indistinguishable for a patient in terms of range of motion.

Further, the first joint section may comprise on each side of the concave joint surface along the first axis a support face extending transverse (preferably perpendicular) to the first axis, each support face including a retaining pin protruding from the support face.

In this case, the second joint section comprises on each side of the circumferential surface an end face extending transverse (preferably perpendicular) to the second axis. In each of the two end faces a retaining groove is formed that extends between (preferably from) the center of the end face up to the circumferential surface.

Preferably, the retaining grooves preferably extend at an angle to the radial direction relative to the second axis.

The retaining pins of the support faces protrude inwards, i.e. they protrude towards each other. In an assembled state, the second joint section is arranged between these retaining pins.

In particular, the second joint section is received or accommodated in a cavity that is formed by the concave joint surface and the support faces of the first joint section facing inwards.

The retaining pins are engageable with the retaining grooves so that the second joint section may be installed and retained in the first joint section as described in the following.

For assembly, the retaining pins of the first joint section are brought into engagement with the retaining grooves of the end faces of the second joint section.

In this stage of assembly, the joint surface of the circumferential surface basically faces towards the same direction as the concave joint surface of the first section (i.e. they do not face each other). Then, the second joint section is moved towards the first joint section guided by the engagement between the retaining pins and retaining grooves so that the second joint section can be turned about the retaining pins. After turning, the joint surfaces of the joint implant face each other.

Since the groove preferably has only one end that extends up to the circumferential surface (i.e. opens up to the circumferential surface), the second joint section is retained in the first section with the joint surfaces facing each other. Thus, in an assembled state, the opening of the grooves at the circumferential surface is basically directed towards the second anchoring section or the concave joint surface. This effectively prevents the joint implant from luxation.

Protection from luxation and unintended disassembly of the first and second joint sections may further be provided by the retaining grooves extending at an angle to the radial direction. In other words, the direction of extension of the groove is not radial relative to the second axis but inclined. If present, the angle of inclination is chosen so that the assembled joint cannot reach a position where the second joint section and the retaining pins of the first joint section may disengage.

Preferably, the first anchoring section and/or the second anchoring section has a plate shape, the surface of the plate having a recess with protrusions and/or recesses, wherein the protrusions and/or recesses are preferably substantially oriented in the direction of the first axis and/or second axis.

A plate according to this disclosure has two major surfaces on opposite sides. The major surfaces of the plate are arranged at a distance due to the thickness of the plate, wherein the thickness of the plate is smaller (preferably at least two, at least three or at least four times) than a width and a length of the plate (width, length, and thickness being perpendicular to each other).

The protrusions and/or recesses preferably have a longitudinal direction that is even more preferably oriented in the direction of the first and/or second axis. The first and second axes are preferably aligned with the width direction of the plate-shaped anchoring sections. In other words, the protrusions and/or recesses are extending substantially perpendicular to the longitudinal direction of the plate.

The advantage of such an orientation of the protrusions and/or recesses is that they are extending in the direction of insertion of the anchoring sections of the joint implant.

In particular, the anchoring section (and, thus, the joint implant) is configured to be inserted from a lateral or medial side of a finger or toe. Further, it is configured to be inserted into a slit having parallel sides that define the width of the slit. Thus, during insertion, the longitudinal direction of the protrusions and/or recesses is preferably guiding the anchoring sections into the slit, i.e. in the depth direction of the slit.

Preferably, the protrusions are integrally formed. The protrusions and/or recesses of an anchoring section may form an undulating pattern on at least one of the major surfaces of an anchoring section.

In other words, the undulating pattern has an undulating profile as seen from the lateral side of an anchoring section (in the width direction) so that the longitudinal extension of the undulating pattern is in the width direction of an anchoring section.

Such an undulating pattern may have a rounded and/or faceted profile. If both major sides of a plate-shaped anchoring section have an undulating pattern, the undulating pattern is preferably in phase, i.e. the profiles of the undulating patterns of these two side basically run parallel to each other.

The surface structure of an anchoring section is configured to assist in causing a press-fit in a slit that has been formed in bone tissue at the end of a bone, where a native joint has been resected. As described above, the slit or recess is introduced into the bone tissue in a lateral direction in order to minimize the impact on the soft tissue structures of the joint to be replaced. This slit has parallel side faces. The distance of these side faces define the width of the slit, i.e. the smallest dimension of the slit. Such a slit is preferably formed using a cutting tool such as a saw or a milling cutter.

When an anchoring section is inserted into the slit, the protrusions are pressed into the side surfaces of the slit. This provides a primary stability to the joint. The press-fit is preferably sufficient to provide an initial stability to the implant directly after implantation without additional means for fixation such as screws, nails, wires or bone cement being necessary for anchoring the joint implant so that it can basically be used directly after implantation.

This movability of the joint implant directly or shortly after implantation is particularly important in order to keep the tendons of the patient intact and to prevent the musculoskeletal system from becoming stiff.

Preferably, the first anchoring section and/or the second anchoring section has a coating, preferably a plasma coating.

The application of a coating, in particular a spray coating, to the first and/or second anchoring section is for enhancing bone ingrowth after implantation. For this reason, preferably a titanium plasma coating is used, i.e. the coating comprises or substantially consists of titanium.

Preferably, the first joint section, the first anchoring section and/or the second anchoring section is made of a metal alloy, in particular a titanium alloy, and the second joint section is made of a metal alloy or a polymer, preferably UHMWPE.

Titanium has been proven to be highly biocompatible. Further, bone ingrowth provides secondary stability to the implant in the weeks after implantation that successively replaces aforenoted primary stability.

Finger joints experience considerable less loads than other artificial joints. Consequently, a metal on metal configuration of the joint surfaces may be used. Nonetheless, preferably a metal on polymer, in particular comprising or consisting of UHMPWE, is used in order to reduce friction and to avoid abrasive metal particles. A polymer on metal configuration also has the advantage to have a low coefficient of friction.

Further, the present disclosure provides in view of abovenoted objective a method for pre-assembling a joint implant for replacing an interphalangeal joint, in particular a joint implant according to any one of the preceding claims. The method comprises the steps of providing a first joint section, the first joint section comprising a concave joint surface about a first joint axis and providing a second joint section, the second joint section comprising a circumferential surface including a convex joint surface about a second joint axis. As a next step the first joint axis and the second joint axis are brought substantially into alignment. The convex joint surface is brought into contact with the concave joint surface for forming a hinge joint.

The step of bringing the convex joint surface into contact with the concave joint surface is preferably a separate step, i.e. it is successively performed (i.e. not at the same time) after the step of initially bringing the first joint axis and the second joint axis substantially into alignment.

Preferably, the assembly is done as a pre-assembly, i. e. an assembly before implantation (i.e. before the implant gets into contact with the patient).

Even more preferably, this pre-assembly is done before delivery. Thus, another one of the advantages of the joint implant of this disclosure is the pre-assembly outside the body of the patient. This is possible due to the lateral insertion of the implant into the opposite bones that remain after the resection of the native joint. In other words, the implant is configured to be inserted in an assembled state.

Preferably, retaining grooves in the end faces of the second joint section are brought into engagement with corresponding retaining pins of the first joint section. This brings the first joint axis and the second joint axis substantially into alignment. Further, for bringing the convex joint surface into contact with the concave joint surface, the first joint section and the second joint section are rotated relative to each other, after the retaining pins and retaining grooves are engaged, until the concave joint surface faces the convex joint surface. In other words, for bringing the convex joint surface of the second joint section and the concave joint surface into contact with each other, the second joint section is rotated about the retaining pins.

As already described in more detail above, this has the advantage that an unintended luxation of the joint implant within the body of a patient can effectively be prevented since the opening of the retaining grooves face towards the concave surface of the first joint section after having rotated the circumferential surface of the second joint section about the retaining pins.

SHORT DESCRIPTION OF THE DRAWINGS

The following figures illustrate preferred embodiments of the present invention. These embodiments are not to be construed as limiting but merely for enhancing the understanding of the invention in context with the following description. In these figures, same reference signs refer to features throughout the drawings that have the same or an equivalent function and/or structure. It is to be noted that a repetitive description of these features is generally omitted for reasons of conciseness.

DETAILED DESCRIPTION OF PREFERRED EMBODIMENTS

Figure 1:
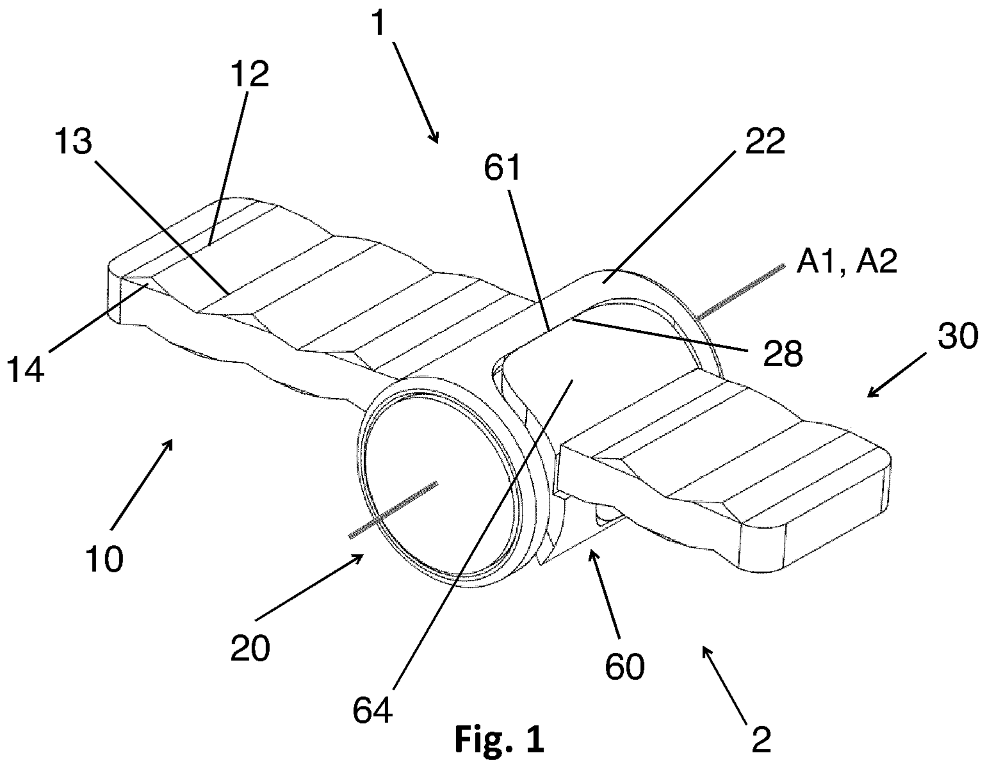
FIG. 1 is a three-dimensional view illustrating an embodiment of an assembled interphalangeal joint implant in extension according to the present disclosure.

In the following, preferred embodiments of an interphalangeal joint implant according to the present disclosure are described under reference to the figures. FIG. 1 illustrates a three-dimensional view of an assembled joint implant for replacing an interphalangeal joint in a finger or foot of a patient.

Figure 2:
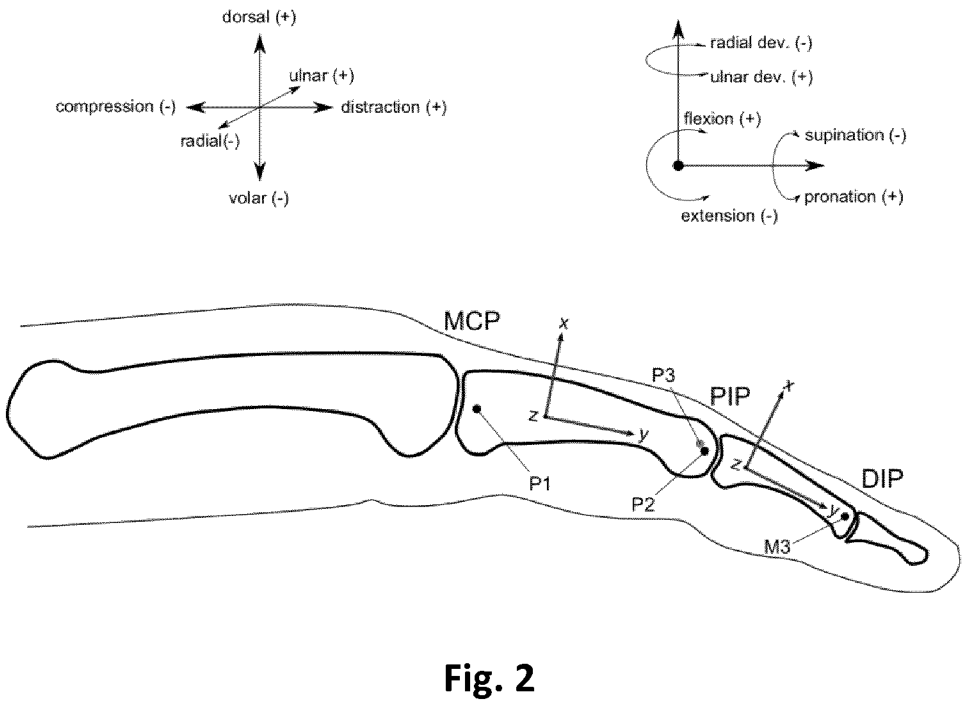
FIG. 2 is a schematic drawing for illustrating the kinematics of an interphalangeal joints of a hand.

The joint implant is configured to be inserted from a lateral or medial side into a space created by resecting an interphalangeal joint. For example, FIG. 2 shows a schematic cross-section of a finger.

The interphalangeal joints are located between any of two adjacent bones of this finger. In case of the finger illustrated in FIG. 2, these interphalangeal joints are the distal interphalangeal joint (DIP), the proximal interphalangeal joint (PIP), and the metacarpophalangeal joint (MCP).

As the skilled person will appreciate, the interphalangeal joints of the foot have a similar configuration. A joint implant according to the present disclosure is inserted laterally, i.e. from the lateral or medial side of an interphalangeal joint that has previously been resected. For example, under reference to FIG. 2, the joint implant is inserted in a direction substantially perpendicular to the plane of this figure.

Returning to FIG. 1, the joint implant is generally configured as a hinge joint. However, as will be explained in the following, this hinge joint has a configuration that also allows for comparatively small movements in rotational (supination/pronation) and/or translational directions (compression/distraction) in order to enhance the adaption of the interphalangeal joint replacement to the kinematic environment of a patient. This kinematic environment is, for example, defined by the arrangement of tendons and muscles. As a result, the interphalangeal joint functions similar to the native joint to be replaced.

The hinge joint illustrated in FIG. 1 comprises a first component 1 and a second component 2. The first component 1 and the second component 2 function as hinge joint, i.e. they rotate relative to each other about a hinge axis (first axis A1 and second axis A2 that are basically aligned during contact of the concave joint surface 21 and the convex joint surface 41).

Figure 3:
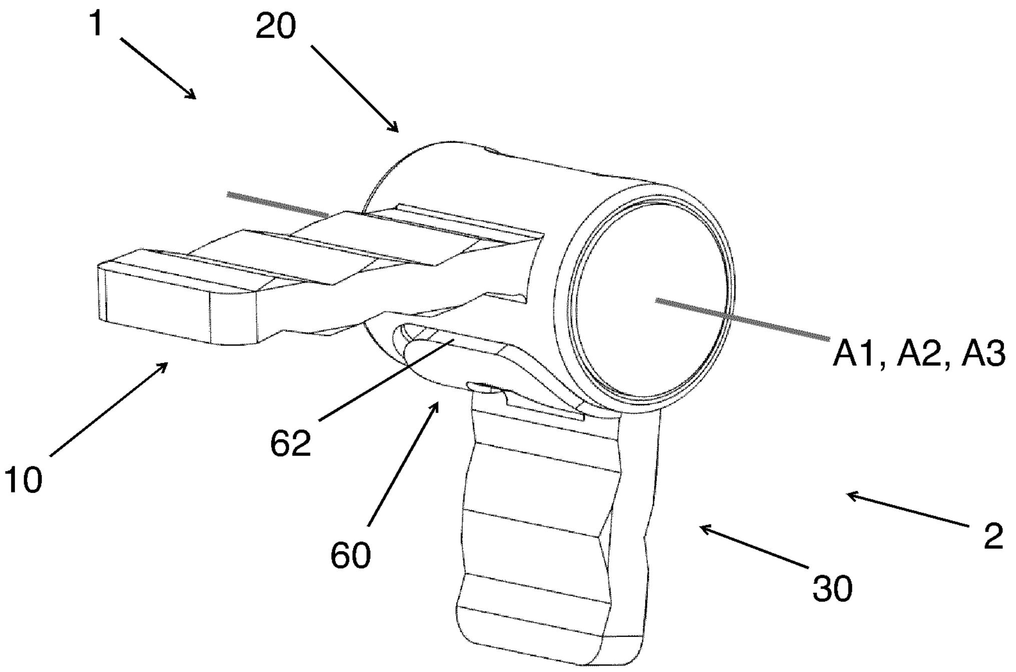
FIG. 3 is a three-dimensional view illustrating the embodiment of the assembled interphalangeal joint implant of FIG. 1 in flexion.

The illustration of the exemplary joint implant according to this disclosure in FIG. 1 shows the joint implant in extension. For comparison, FIG. 3 shows the joint implant of FIG. 1 at rotational position in flexion at about 105°. The angular range between extension and maximum flexion defines the range of motion of the interphalangeal joint implant. Preferably, the range of motion of such a joint implant is 0° to 110°, preferably 0° to 100°, or 0° to 90°.

Even more preferably, these ranges of motion start from an angle larger than 0°, i.e. an angle slightly larger than the angle of complete extension (at 0°). For example, the range of motion may start at an angle of 1°, 2°, 5°, or 10°. This serves to prevent an overextension of the finger joint implant.

As illustrated in FIG. 1, the first (preferably proximal) component 1 comprises a first anchoring section 10 and a first joint section 20. The second (preferably distal) component 2 comprises a second anchoring section 30 and a second joint section 40 (see FIGS. 3 and 4).

The anchoring section 10 of the first component 1 is preferably integrally formed with the first joint section 20.

In other words, the first anchoring section 10 and the first joint section 20 are connected by a material bond (e.g. by welding, soldering, bonding, etc.) or are fabricated as one-piece (e.g. by casting, sintering, 3D-printing, etc.).

As described above, the second component 2 comprises a joint section 40 and an anchoring section 30. A bone shield 60 is arranged between the joint section 40 and the anchoring section 30.

As described above, the anchoring section 30 and the bone shield 60 are preferably integrally formed. The same may apply to the connection between the bone shield 60 and the second joint section 40.

However, the bone shield 60 and the second joint section 40 are, as illustrated, preferably connected by a compensation mechanism 50 that allows for a translational and/or rotational movability between these two components as will be described further below in more detail.

One of the advantages of a joint implant according to the present disclosure is the insertion of this joint implant from a lateral or medial side of an interphalangeal joint.

As illustrated for the exemplary embodiment of a joint implant in FIG. 1, the anchoring sections 10, 30 preferably have a plate shape.

Further, any one or both of the anchoring sections 10, 30 may be formed with at least one major surface (i.e. larger surface of the anchoring section) having a structure. The structured surface may be structured on a macro scale and/or a micro scale.

As visible from the figures, the shape of the structured surface on a macro scale is defined by recesses 13 and protrusions 12. The recesses 13 and protrusions 12 preferably form an undulating or wave-like structure. More specifically, in a proximal-distal cross-section of the anchoring section 10, 30 (perpendicular to the first joint axis A1 or ulnar-radial direction as shown in FIG. 2), at least one of the major surfaces has a wave-like or undulating profile.

This undulating profile of the anchoring section 10, 30 particularly extends laterally, i.e. in the direction of the anchoring section's width.

In other words, the recesses 13 and protrusions 12 extend in the width direction of the anchoring section 10, 30, i.e. the width direction (lateral direction) of the implant.

The recesses 13 provide guidance when laterally implanting the anchoring section 10, 30 of the (assembled) joint implant into a substantially equidistant slit that has been prepared in a phalangeal bone.

Accordingly, the anchoring sections 10, 30 of the joint sections are preferably configured to be implanted into a slit. The side surfaces of such a slit are substantially at a fixed distance (i.e. slit width).

The depth of the slit extends in a lateral direction of the phalangeal bone (Z-direction or radial-ulnar direction in FIG. 2) and corresponds to the direction of insertion and lateral direction of the joint implant.

The slit within the bone tissue is at least opening towards one of the lateral sides and the face side of the phalangeal bone, where the native interphalangeal joint has been resected.

Preferably, at least three and preferably all of the protrusions 12 define a plane, i.e. their ends in a direction perpendicular to the plate-shaped anchoring sections 10, 30 are arranged in one plane. The same preferably also applies to the recesses 13. Nonetheless, other shapes are also possible such as regular or irregular arranged protrusions that define one or multiple planes.

As a result, the protrusions 12 all have substantially the same amount of contact with the side surface of a slit that has been prepared in the bone tissue of a phalangeal bone for anchoring the joint implant.

More specifically, the anchoring sections 10, 30 are pressed laterally into slits that have been prepared in the ends of two adjacent phalangeal bones that face each other. Since ends or tips of the protrusions 12 are arranged on a plane, they will exert approximately the same pressure onto the adjacent bone tissue of a slit's side wall.

The height between a recess 13 and a protrusion 12 is preferably chosen so that the opposing bone tissue of a slit's side surface is primarily elastically deformed. In other words, the height is chosen so that the deformation of the slit's side surface upon entrance of the protrusion 12 is at least primarily elastic. As a result, the press-fit between the joint implant and the bone tissue is enhanced since a reduction in contact pressure due to damage to the bone tissue is avoided.

Further and for guidance during insertion of the joint implant as well as for avoiding damage to the bone tissue, the lateral ends of the protrusions 12 and/or recesses 13 in relation to the anchoring sections 10, 30 are preferably provided with chamfers 14.

The chamfers are at least provided to the lateral side of the anchoring section 10, 30 that faces the phalangeal bone prior and during insertion of the implant. During insertion of the anchoring section 10, 30 the chamfer acts like a wedge gradually bringing the protrusions 12 of the anchoring section 10, 30 into engagement.

This facilitates an insertion of the implant and makes the process of insertion more stable. In particular, the chamfer helps to prevent the anchoring section from tilting away when pressure is laterally applied to the plate-shaped anchoring section 10, 30 for pressing the anchoring section 10, 30 into the slit of a phalangeal bone.

The undulating profile of the macro structure also has the advantage to prevent the implant from slipping out of the bone tissue in a proximal-distal direction of the phalangeal bone.

More specifically, the protrusions pressing into the bone tissue and having an extension in the lateral direction of the anchoring section 10, 30 prevent the anchoring section 10, 30 from being pulled out of the bone. In this respect, it is preferred that both major surfaces of an anchoring section 10, 30 have an undulating profile in a lateral cross-section. Such a configuration renders an anchoring section more elastic, which can provide a press-fit that adapts to differences in bone density along the slit.

Even more preferably, the undulating profiles of the opposite major surfaces of the plate-shaped anchoring section 10, 30 are basically extending along the anchoring section 10, 30 in a proximal-distal direction in parallel so that on the side opposite of a protrusion 12 (i.e. at the same location in the proximal-distal direction of the implant but on the other or opposite major surface) is a recess 13 and vice versa (see FIGS. 1, 3, 5, and 6). This results in the surface of a lateral edge (side edge) of such an anchoring section 10, 30 having an undulating shape.

The undulating surface structure may be faceted as shown in the figures, i.e. it is formed by planar surfaces that are angled in relation to each other. Alternatively, or additionally, the undulating surface structure may be curved. For example, the protrusions 12 and/or recesses 13 may have rounded maxima and/or minima, respectively. The undulating surface structure may also be curved with planar minima and/or planar maxima. Also, the undulating surface structure may have a continuously curved profile.

The undulating surface structure may be regular or irregular, i.e. the protrusions 12 and recesses 13 are formed in the proximal-distal direction of the implant at regular or irregular distances from each other.

This is advantageous for different bone densities along an anchoring section. For example, smaller distances may be used for an area with primarily spongious bone tissue and larger distances may be used for an area with primarily cortical bone tissue.

As described above, the macro structure improves the primary stability of the implant after insertion. In other words, the macro structure helps in preventing a relative movement between the bone tissue of an interphalangeal bone and the surface of an anchoring section 10, 30. This stability in anchoring improves the conditions for a permanent fixation of the joint implant by bone in growth, the so-called secondary stability.

For enhancing the secondary stability, at least a part of the surface of the anchoring sections 10, 30 preferably includes a microstructure. This microstructure fosters bone ingrowth by providing a surface that supports the creation of bone tissue by osteoblasts. As already described above, such a surface is preferably provided using a plasma spray coating, in particular a titanium plasma spray coating. Nonetheless, other techniques such as 3D printing may be used to create a surface structure for enhancing bone ingrowth. These surface structures are preferably porous surface structures.

Returning to FIG. 1, the bone shield 60 of the second component 2 may comprise a bone shield abutment surface 61 that limits the range of motion in extension. More specifically, the bone shield abutment surface 61 abuts or gets into contact with an abutment surface 28 of the first joint section 20 if the joint implant is in extension.

Likewise, the bone shield 60 may have an abutment surface 62 that faces into the opposite circumferential direction to the abutment surface 61. This abutment surface 62 faces and abuts an abutment surface 27 of the first joint section 20 when the joint implant is positioned in maximum flexion (see FIGS. 3 and 6).

The outer surface 22 of the first joint section 20 is preferably substantially flush with the outer surface 64 of the bone shield 60. This is particularly illustrated in FIG. 1, in which the joint implant is in maximum extension and the abutment surface 61 of the bone shield 60 is in contact with the abutment surface 28 of the first joint section 20.

Figure 4:
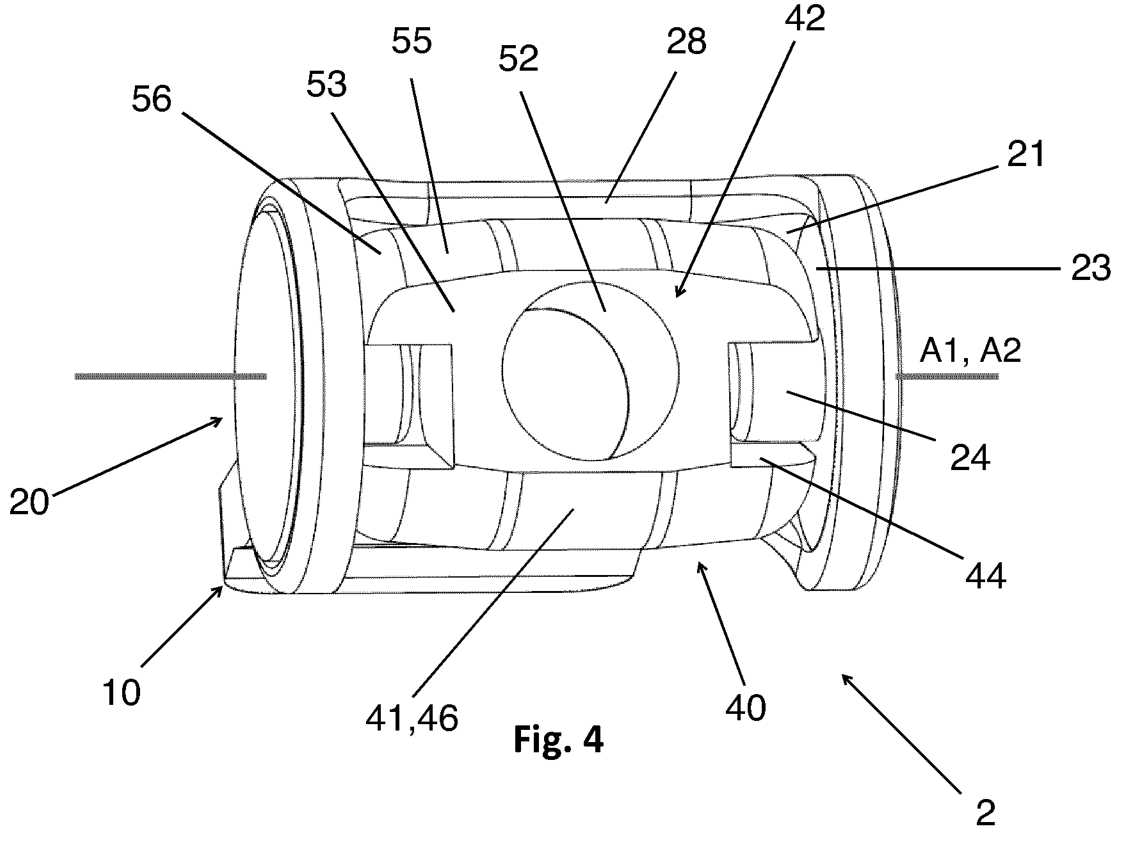
FIG. 4 is a three-dimensional view of the interphalangeal joint implant in a partly assembled state.

Turning to FIG. 4, this figure shows a detailed view of the second joint section 40 being installed within the recess of the first joint section 20 so that the first joint axis A1 of the first joint section 20 is aligned with the second joint axis A2 of the second joint section 40. These axes A1, A2 are aligned if the convex joint surface 41 of the second joint section 40 is in contact with the concave joint surface 21 of the first joint section 20.

As shown in FIG. 4, a recess of the first joint section 20 for accommodating the second joint section 40 is formed by the concave joint surface 21 and two support faces 23 located at the ends of the concave joint surface 21 in the lateral direction of the joint implant. The concave joint surface 21 has a circular profile in a cross-section perpendicular to the second joint axis A2 forming the female surface of the hinge joint. Preferably, the concave joint surface 21 has at least a constant radius in its central portion that interacts with the convex joint surface 41 of the second joint section 40, i.e. the part of the circumferential surface of the second joint section 40 that forms the male surface of the hinge joint. Even more preferably, the concave joint surface has a circular cylindrical shape.

Figure 6:
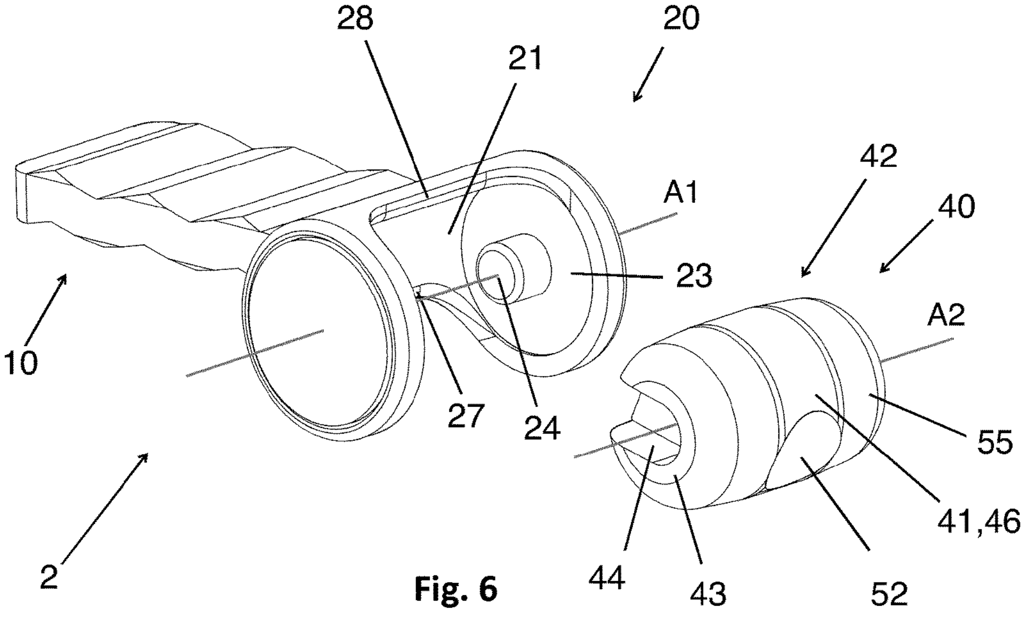
FIG. 6 is a three-dimension exploded view for showing an assembly of a first and a second joint section in more detail.

As illustrated in FIGS. 4 and 6, a retaining pin 24 may protrude from each of the support faces 23 into aforenoted recess formed by the concave joint surface 21 and the support faces 23.

Consequently, these retaining pins 24 are located on opposite sides and face each other. Preferably, the retaining pins 24 are cylindrical and in particular circular cylindrical. They preferably protrude perpendicular to the support faces 23 along and aligned with the first joint axis A1 of the first component 1.

Turning to the second joint section 40, the joint section 40 is generally formed as a solid of revolution. Nonetheless, as will be explained below in more detail in relation to the compensation mechanism 50, the second joint section 40 preferably has a flat joint section abutment surface 53 and a hole 52.

This flat joint section abutment surface 53 forms part of the circumferential surface 42 of the second joint section 40. The hole 52 for receiving a pin 51 of the compensation mechanism 50 has an opening in the joint section abutment surface 53 (see FIG. 4) and preferably an opening on the opposite side facing the concave joint surface 21 of the first joint section 20.

At each of the two ends along the second joint axis A2, the second joint section 40 comprises an end face 43 and a retaining groove 44. The second joint axis A2 defines the central axis of the convex joint surface 41 and is the axis of symmetry of the solid of revolution generally forming the second joint section 40.

As illustrated in the figures, the second joint section 40 is preferably barrel-shaped. In other words, the circumferential surface 42 of the second joint section 40 comprises a central portion along the second joint axis A2 having a circular outer cross-section (except for the joint section abutment surface that is preferably flat). This circular cross-section defines a cylindrical section 46, which forms the convex joint surface 41.

At least on one side but preferably on both sides of this cylindrical section 46 are tapered sections 55. The transition between the circular cylindrical section 46 and the tapered section(s) 55 is preferably rounded, i.e. continuous, in order to prevent stress concentrations that may otherwise occur at an edge formed between the cylindrical section 46 and a tapered section 55.

For the same reason, the transition between the tapered sections 55 and the end faces 43 of the second joint section 40 is formed by a rounded section 56 having a rounded surface that connects a tapered section 55 and an end face 43. Here too, the transition between the tapered sections and the rounded surface is preferably continuous to avoid stress concentrations upon loading of the joint.

As a result of this configuration of the second joint section 40, the concave joint surface 21 may only be contact with the corresponding convex joint surface 41 in a central portion of the joint along the joint axes A1, A2.

Further, due to the reduced diameters of the tapered sections 55 and the rounded transition sections 56, a gap is formed between the preferably cylindrical concave joint surface 21 of the first joint section 20 and the circumferential surface 42 of the second joint section 40. This gap provides space for joint liquid and, thus, helps in stabilizing a fluid film between the concave joint surface 21 and the convex joint surface 41 in an implanted state of the joint implant. This fluid film reduces the friction in the hinge joint of the implant and, thus, enhances its service life.

As previously described, the retaining pins 24 of the first joint section 20 and the retaining grooves 44 of the second joint section 40 interact with each other. During assembly, the second joint section 40 is moved into the recess formed by the concave joint surface 21 with the portion of the circumferential surface 42 that after assembly functions as convex joint surface 41 facing into the same direction as the concave joint surface 21 (see FIG. 6). In other words, the second joint section is offset about the second joint axis A2 by approximately 180° during assembly in relation to its orientation in extension of the joint implant after assembly.

This results in the end of the retaining grooves 44 at the circumferential surface 42 facing the retaining pins 24 so that the retaining pins 24 of the first joint section 20 can enter and engage the retaining grooves 44 of the second joint section 40. As shown in the figures, the other end of the retaining grooves 44 is preferably located approximately in the center of the end face 43 so that the retaining pins 24 are positioned in the retaining grooves 44 in the assembled state of the joint, while the joint axes A1 and A2 are aligned (and the concave joint surface 21 is in contact with the convex joint for surface 41).

As described above, the joint implant may further comprise a compensation mechanism 50 that preferably acts between the second joint section 40 and the bone shield 60 including the second anchoring section 30. The compensation mechanism 50 is configured to compensate forces acting in a proximal-distal direction of the joint implant and/or torque that acts about the longitudinal axis of the joint implant.

The compensation mechanism 50 comprises a translational and/or rotational joint that keeps forces and/or torque acting between the second anchoring section 30 and the second joint section 40 from being transferred.

It is assumed that the loads and the torque that is compensated for by a movement of this compensatory joint of the compensation mechanism 50 at least partly exist due to differences between the artificial hinge joint and a native interphalangeal joint. These differences may also be caused upon implantation of the joint implant, for example by an alignment of the implant between the two opposing phalangeal bones that, for example, results in the rotational axis of the joint implant being different from the joint axis of the native interphalangeal joint that has been resected. Further, the muscles and tendons surrounding the interphalangeal joint implant may cause differences due to their location after implantation. Here, the compensation mechanism 50 at least helps in overcoming these differences so that an adverse effect thereof onto the longevity of the interphalangeal joint implant can be avoided.

The compensation mechanism 50 is configured to adjust or change the relative position and/or orientation between the second joint section 40 and the bone shield 60 with the second anchoring section 30 instead of transferring forces and/or torque acting along and about the longitudinal axis, respectively. Thus, loads that previously have been transferred via the joint surfaces of the hinge joint are reduced, which has a positive effect on the lifespan of the joint implant.

The exemplary interphalangeal joint implant according to the present disclosure shown in the figures is configured for compensating both between the second joint section 40 and the second anchoring section 30, i.e. longitudinal forces acting along the fourth joint axis A4 as well as rotational forces (i.e. torque) acting about the fourth joint axis A4.

This is achieved by the compensation mechanism 50 being configured as a joint with these 2 degrees of freedom.

Figure 5:
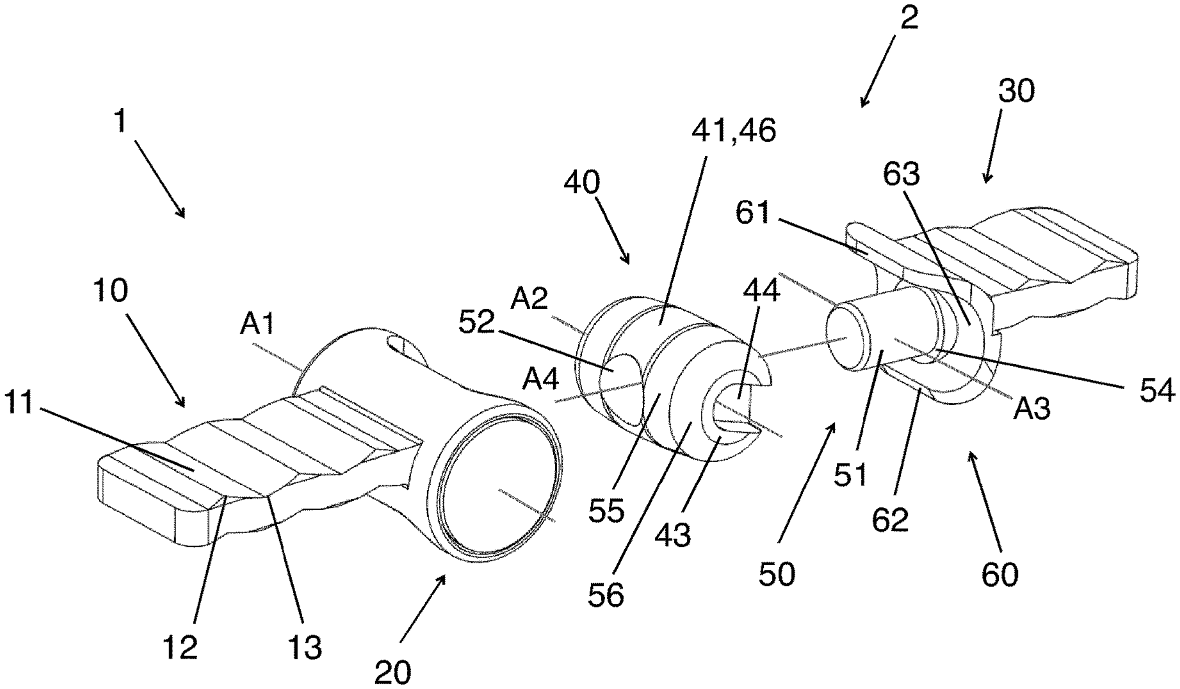
FIG. 5 is three-dimensional exploded view of an interphalangeal joint implant for illustrating an embodiment of a compensatory mechanism.

As particularly illustrated in FIG. 5, this joint comprises a pin 51 that protrudes along and is preferably aligned with the fourth joint axis A4. The pin protrudes from the inner surface 63 of the bone shield 60 and is preferably integrally formed. This figure further illustrates that the pin comprises a base portion having a larger diameter than the pin 51 so that a step is formed between this base portion and the pin 51.

This step includes an annular surface that faces the second joint section 40 and in particular the preferably flat joint section abutment surface 53 and acts as an anchoring section abutment surface 54, as will be explained in more detail further below.

In order to allow for a rotational and translational movement, the pin 51 preferably has a cylindrical shape with a circular cross-section. Preferably, the pin 51 and its base portion is integrally formed with the bone shield 60 and/or the anchoring section 30.

As already noted above, the second joint section 40 includes a hole 52 functionally belonging to the compensation mechanism 50 that corresponds to the pin 51 protruding from the bone shield 60 in order to function as a translational and rotational joint. As described above, the hole 52 of the compensation mechanism 50 is preferably formed as a through hole in order to allow for a smooth translational movability of the pin 51 into and out of the hole 52. More specifically, in the environment of the hole 52 and the pin 51 will be joint liquid in an implanted state. By configuring the hole 52 as a through hole, any liquid present in front of the face side of the pin 51 will be able to escape through the end of the through hole 52 that faces the concave joint surface 21 of the first joint section 20.

Nonetheless, the hole 52 may also be configured as a blind hole in order to achieve a dampening effect for the relative movement between the second anchoring section 30 and the second joint section 40 in the translational direction along the fourth joint axis A4.

If a compensation mechanism 50 is present, aforenoted gap between the inner surface 63 of the bone shield 60 and the circumferential surface 42 of the second joint section 40 may not only assist in lubricating the hinge joints but may further serve for the compensation mechanism 50 being able to perform a relative rotation about the fourth joint axis A4 if the pin 51 is at an end position within the hole 52.

In this end position, the anchoring section abutment surface 54 of the pin 51 is in contact with the joint section abutment surface 53 of the second joint section 40. In extension of the joint implant, the joint section abutment surface 53 is arranged to substantially face into the same direction as the concave joint surface 21 of the first joint section 20 in the assembled state of the implant (cf. FIG. 5).

In order for the compensation mechanism 50 to be able to rotate in this end position, there is particularly a wedge like gap between the tapered sections 55 and the inner surface 63 of the bone shield 60.

In other words, at both ends of the joint section 40 and the bone shield 60 (at least at one of their ends) the gap between the inner surface 63 and the tapered section 55 increases in width.

Further, for a smooth rotation about the fourth joint axis A4, there is preferably also a gap present in the central portion along the third joint axis A3 that faces the cylindrical section 46 the second joint section 40.

Alternatively, the outer surface 42 of the second joint section 40 may be curved at the cylindrical section 46 in a cross section along the second joint axis A2 to allow for such a smooth rotation.

Further, the inner surface 63 of the bone shield 60 may also be curved. For example, the inner surface 63 has a radius that is larger than a radius of the outer surface 42. The outer circumferential surface 42 of the joint section 40 preferably has a higher curvature than the inner surface 63 of the bone shield 60, in particular for allowing for above-noted smooth rotation about the fourth joint axis A4.

Due to the presence of this gap, the second anchoring section 30 is able to rotate about the fourth joint axis A4 and relative to the second joint section 40 in afore-noted end position with an abutment of the joint section abutment surface and the anchoring section abutment surface. This relative rotation has a range of motion in aforenoted ranges that is limited due to the inner surface 63 of the bone shield 60 getting into contact with the inclined surfaces of the tapered sections 55 (depending on the configuration of the tapered section, these inclined surfaces may be linear or curved). This contact is preferably configured as a line contact or a surface contact of the inner surface 63 with the surface of the tapered sections 55 in order to avoid stress concentrations during an abutment of these surface.

If such a compensation mechanism 50 is included in an interphalangeal joint according to the present disclosure, the kinematic behavior of the joint is closer to the kinematic behavior of a native interphalangeal joint since it does not only allow a rotation about the hinge joint axis A1, A2 but also a rotation about the fourth joint axis A4 in aforenoted ranges.

This is achieved in a defined movement of the individual joints that prevents the feeling of a wobbly joint. Instead, the interphalangeal joint implant provides the stable impression of a native joint. In other words, an interphalangeal joint implant with such a compensation mechanism mimics the anatomic rotational-sliding movement of a native joint.

REFERENCE SIGNS

The following lists the reference signs used in the description and the drawings. Throughout the drawings these reference signs refer to features that have the same or an equivalent function and/or structure.

1 first component
2 second component
10 first anchoring section
11 surface structure
12 protrusion of surface structure
13 recess of surface structure
14 chamfer of surface structure
20 first joint section
21 concave joint surface
22 outer surface of the first joint section
23 support face
24 retaining pin
27 abutment surface in flexion
28 abutment surface in extension
30 second anchoring section
40 second joint section
41 convex joint surface
42 circumferential surface
43 end face
44 retaining groove
46 cylindrical section of/forming convex joint surface
50 compensation mechanism
51 pin of compensation mechanism
52 hole of compensation mechanism
53 joint section abutment surface
54 anchoring section abutment surface

55 tapered section
60 bone shield
61 bone shield abutment surface in extension
62 bone shield abutment surface in flexion
63 inner surface of the bone shield
64 outer surface of the bone shield
A1 first joint axis
A2 second joint axis
A3 central axis of bone shield
A4 translational axis of longitudinal compensation mechanism

The invention claimed is:

1. A joint implant configured to replace an interphalangeal joint, comprising:

a first component, wherein the first component comprises a first joint section and a first anchoring section, the first joint section including a concave joint surface about a first axis and the first anchoring section extending transverse to the first axis; and a second component, wherein the second component comprises a second joint section and a second anchoring section, the second joint section including a circumferential surface about a second axis and the second anchoring section extending transverse to the second axis, wherein the circumferential surface comprises a convex joint surface that is configured to act as a hinge joint with the concave joint surface of the first joint section;

the second component further comprising a bone shield arranged between the second joint section and the second anchoring section, wherein the bone shield extends about a third axis and partially covers the circumferential surface of the second joint section with a gap being formed between the circumferential surface and the bone shield, wherein the bone shield forms at least one abutment surface facing in a circumferential direction in relation to the third axis, wherein the bone shield is configured to limit flexion or extension of the joint implant.

2. The joint implant according to claim 1, wherein the second joint section is connected to the bone shield via a compensation mechanism, the compensation mechanism configured to allow a relative movement between the second joint section and the bone shield in relation to a fourth axis, the fourth axis being transverse to the second axis of the second joint section.

3. The joint implant according to claim 2, wherein the compensation mechanism comprises a pin and a hole, wherein the pin and the hole are configured for a relative movement along and/or about the fourth axis (A4).

4. The joint implant according to claim 2, wherein along the second axis, the convex joint surface is arranged in a middle portion and in between two tapered sections of the circumferential surface, wherein the tapered sections are configured to limit the relative rotation of the bone shield and the second joint section about the fourth axis.

5. The joint implant according to claim 4, wherein the relative rotation of the bone shield and the second joint section about the fourth axis is limited to about ±2° to ±10°.

6. The joint implant according to claim 1, wherein the gap is formed between the circumferential surface of the second joint section and an inner surface of the bone shield by a difference in their profiles.

7. The joint implant according to claim 1, wherein a profile of the circumferential surface in a cross-section along the second axis is faceted.

8. The joint implant of claim 1, wherein a range of motion of the joint implant in flexion-extension is approximately 90° to 110°.

9. The joint implant according to claim 1, wherein the first joint section comprises, on each side of the concave joint surface along the first axis, a support face extending transverse to the first axis, each support face including a retaining pin protruding from the support face, and wherein the second joint section comprises, on each side of the circumferential surface, an end face extending transverse to the second axis, wherein in each end face a retaining groove is formed between the center of the end face up to the circumferential surface, the retaining grooves extending at an angle to the radial direction relative to the second axis.

10. The joint implant according to claim 1, wherein the first anchoring section and/or the second anchoring section has a plate shape, the surface of the plate having a surface structure with protrusions and/or recesses, wherein the protrusions and/or recesses are oriented in the direction of the first and second axes.

11. The joint implant according to claim 1, wherein the first anchoring section and/or the second anchoring section has a plasma coating.

12. The joint implant according to claim 1, wherein the first joint section, the first anchoring section and/or the second anchoring section is made of a metal alloy, and the second joint section is made of a material selected from the group consisting of a metal alloy, a polymer, and UHMWPE.

13. A joint implant configured to replace an interphalangeal joint, comprising:

a first component, wherein the first component comprises a first joint section and a first anchoring section configured to engage a first bone, the first joint section including a concave joint surface about a first axis and the first anchoring section extending transverse to the first axis; and a second component, wherein the second component comprises a second joint section and a second anchoring section configured to directly engage a second bone, the second joint section including a circumferential surface about a second axis and the second anchoring section extending transverse to the second axis, wherein the circumferential surface comprises a convex joint surface that is configured to act as a hinge joint with the concave joint surface of the first joint section;

the second component further comprising a bone shield arranged between the second joint section and the second anchoring section, wherein the bone shield extends circumferentially about a third axis and partially covers the circumferential surface of the second joint section with a gap being formed between the circumferential surface and the bone shield, wherein the bone shield comprises an outer surface from which the second anchoring section integrally extends in a direction transverse to the third axis.

14. The joint implant according to claim 13, wherein the gap between the circumferential surface of the second joint section and an inner surface of the bone shield provides a space configured to act as a reservoir for synovial fluid to assist in lubricating the joint implant.

15. The joint implant according to claim 13, wherein the gap increases in width towards ends of the bone shield along the third axis.

16. The joint implant according to claim 13, wherein the bone shield comprises two abutment surfaces facing in opposite circumferential directions, wherein one abutment surface limits flexion and another abutment surface limits extension of the joint implant.

17. The joint implant according to claim 13, wherein the second joint section is connected to the bone shield via a compensation mechanism, the compensation mechanism configured to allow a relative movement between the second joint section and the bone shield in relation to a fourth axis, the fourth axis being transverse to the second axis of the second joint section, wherein along the second axis, the convex joint surface is arranged in a middle portion and in between two tapered sections of the circumferential surface, wherein the tapered sections are configured to limit the relative rotation of the bone shield and the second joint section about the fourth axis, and wherein the tapered sections are configured for a line contact or a surface contact with an inner surface of the bone shield to reduce contact pressure at a stop position.

18. The joint implant according to claim 13, wherein the first anchoring section and/or the second anchoring section has a plate shape, the surface of the plate having a surface structure with protrusions and/or recesses, wherein the protrusions and/or recesses are oriented in the direction of the first and second axes, and wherein the protrusions define a plane such that ends of the protrusions in a direction perpendicular to the plate-shaped anchoring section are arranged in one plane.

* * * * *